US008463374B2

(12) United States Patent
Hudson et al.

(10) Patent No.: US 8,463,374 B2
(45) Date of Patent: Jun. 11, 2013

(54) METHOD, SYSTEM AND COMPUTER PROGRAM PRODUCT FOR CONTROLLING COMPLEX RHYTHMIC SYSTEMS

(75) Inventors: John L. Hudson, Charlottesville, VA (US); István Z. Kiss, St. Louis, MO (US); Craig G. Rusin, West Seneca, NY (US); Hiroshi Kori, Tokyo (JP)

(73) Assignee: University of Virginia Patent Foundation, Charlottesville, VA (US)

( * ) Notice: Subject to any disclaimer, the term of this patent is extended or adjusted under 35 U.S.C. 154(b) by 546 days.

(21) Appl. No.: 12/665,458

(22) PCT Filed: Jun. 27, 2008

(86) PCT No.: PCT/US2008/068538
§ 371 (c)(1),
(2), (4) Date: Dec. 18, 2009

(87) PCT Pub. No.: WO2009/003161
PCT Pub. Date: Dec. 31, 2008

(65) Prior Publication Data
US 2010/0198090 A1    Aug. 5, 2010

Related U.S. Application Data

(60) Provisional application No. 60/937,595, filed on Jun. 28, 2007, provisional application No. 61/054,861, filed on May 21, 2008.

(51) Int. Cl.
*A61B 5/00* (2006.01)
(52) U.S. Cl.
USPC .............................................. 607/2; 369/47.1

(58) Field of Classification Search
USPC .............................................. 607/9, 11, 17, 2
See application file for complete search history.

(56) References Cited

U.S. PATENT DOCUMENTS 3,984,675 A * 10/1976 Corcoran et al. ............. 359/244
6,453,198 B1 * 9/2002 Torgerson et al. ............... 607/29
6,658,287 B1 * 12/2003 Litt et al. ....................... 600/544
(Continued)

FOREIGN PATENT DOCUMENTS
WO    0147202 A2    6/2001
WO    03077985 A1   9/2003

OTHER PUBLICATIONS

Kemao et al: "Smoothing Filters in Phase-Shifting Interferometry" Optics and Laser Technology, vol. 33, No. 8, pp. 649-654; (2003).

(Continued)

*Primary Examiner* — Christopher D Koharski
*Assistant Examiner* — Michael Carey
(74) *Attorney, Agent, or Firm* — Robert J. Decker

(57) ABSTRACT

A method, apparatus, and computer program product for controlling the behavior of complex rhythmic systems, such as the nervous system, is disclosed. Robust, engineering based measurements of the rhythmic system are taken and used to generate feedback that guides the system towards a desired state. This methodically designed feedback allows the system to maintain the normal behavior of individual elements, thereby achieving high effectiveness, while at the same time minimizing side effects. It therefore becomes possible to move the system towards the desired state in a non-destructive manner. This approach also allows for increased flexibility and applicability because the feedback is generated in a manner that is tailored to the unique variables of the particular system.

51 Claims, 8 Drawing Sheets

U.S. PATENT DOCUMENTS

| | | | |
|---|---|---|---|
| 6,961,618 B2 * | 11/2005 | Osorio et al. | 607/45 |
| 7,078,903 B2 * | 7/2006 | Paliwal et al. | 324/319 |
| 7,146,218 B2 | 12/2006 | Esteller et al. | |
| 7,209,787 B2 | 4/2007 | DiLorenzo et al. | |
| 2005/0124848 A1 | 6/2005 | Holzner et al. | |
| 2005/0157814 A1 | 7/2005 | Cova et al. | |

OTHER PUBLICATIONS

Tass: "Synergistics of the Nervous System: from Basic Principles to Therapy" Nonlinear Phenomena in Complex Systems, 5(4), pp. 470-478 (2002).

Tass: "A model of desynchronization deep brain stimulation with a demand-controlled coordinated reset of neural subpopulations." Biological Cybemetics 69 (2): 81-88 (2003).

Oleksandr V. Popovych, Christian Hauptmann, and Peter A. Tass, "Effective Desynchronization by Nonlinear Delayed Feedback", Phys. Rev. Lett. 94, 164102 (2005).

Oleksandr V. Popovych • Christian Hauptmann, Peter A. Tass, "Control of neuronal synchrony by nonlinear delayed feedback" Biol. Cybern. 95: 69-85 (2006).

Christini, et al. "Mapping and Control of Complex Cardiac Arrhythmias" Chaos, vol. 12, No. 3, pp. 732-739 (2002).

Reppert, et al. "Coordination of Circadian Timing in Mammals", Nature, vol. 418, pp. 935-941 (2002).

G. Laurent "Olfactory Network Dynamics and the Coding of Multi-dimensional Signals" Nature, vol. 3, pp. 884-895 (2002).

Uhlhaas et al. "Neural Synchrony in Brain Disorders: Relevance for Cognitive Dysfunctions and Pathophysiology" Nature Rev. Neuron, vol. 52, pp. 155-168 (2006).

Allessie, et al. "Circus movement i rabbit atrial muscle as a mechanism of tachycardia, III. The leading circle concept: a new model of circus movement in cardiac tissue without the involvement of an anatomical obstacle" Circulation Research, vol. 41, pp. 9-18 (1977).

Zhai, et al. "Emerging Coherence of oscillating Chemical Reactions on Arrays: Experiments and Simlations" Ind. Eng. Chem. Res., vol. 43, pp. 315-326 (2004).

Kiss, et al. "Emerging Coherence ina Population of Chemical Oscillators" Science. vol. 298, pp. 1676-1678 (2002).

Rosenblum, et al. "Delayed Feedback suppression of Collective Rhythmic Aotivity in a Neuronal Ensemble" International Journal of Bifurcation and Chaos, vol. 16, No. 7, pp. 1989-1999 (2006).

Kiss, et al. "Predicting Mutual Entrainment of Oscillators with Experiment-Based Phase Models"Physical Review Letters, PRL 94, pp. 248301-1 through 248301-4 (2005).

Kiss, et al. "Engineering Complex Dynamical Structures: Sequential Patterns and Desynchronization" Science, vol. 316, pp. 1896-1889 (2007).

Izhikevich, et al. "Class 1 Neural Excitability, Conventional Synapses, Weakly Connected Networks, and Mathematical Foundations of Pulse-Couple Models" IEEE Transactions on Neural Networks, vol. 10, No. 3, pp. 499-507 (1999).

Llinas, et al. "Electrophysiology of Mammalian Thalamic Neurones In Vitro" Nature, vol. 297, pp. 406-408 (1982).

Joliot, et al. "Central Motor Loop Oscilations in Parkinsonian Renting Tremor Revealed by Magnetoencephalography" American Academy of Neurology, vol. 46, pp. 1359-1370 (1996).

McIntyre, et al. "Uncovering the Mechanism(s) of Action of Deep Brain Stimulation: activation, inhibition or Both" Clinical Neurophysiology, vol. 115, pp. 1239-1248 (2004).

* cited by examiner

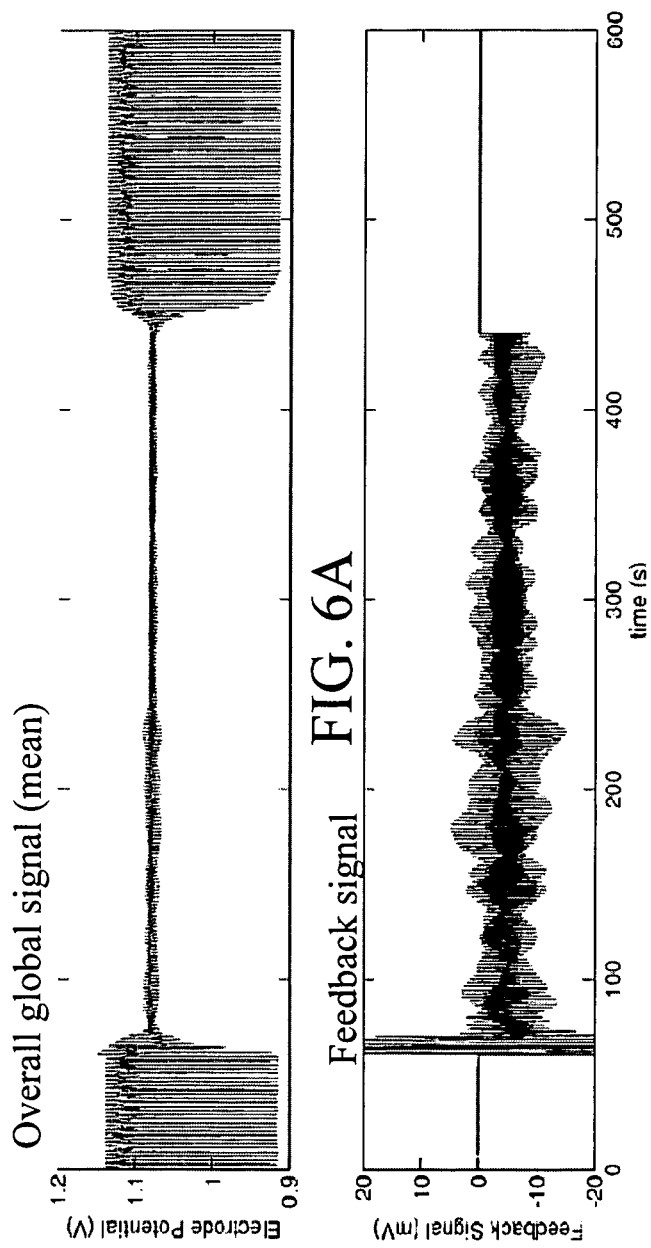

METHOD, SYSTEM AND COMPUTER PROGRAM PRODUCT FOR CONTROLLING COMPLEX RHYTHMIC SYSTEMS

RELATED APPLICATIONS

The present application is a national stage filing of International Application No. PCT/US2008/068538, filed Jun. 27, 2008, which claims priority under 35 U.S.C. §119(e) from U.S. Provisional Application Ser. No. 60/937,595, filed Jun. 28, 2007, entitled "Mild Stimulation Device and Measurement Based Design Method for Non-Destructive Control of Complex Rhythmic Systems" and U.S. Provisional Application Ser. No. 61/054,861, filed May 21, 2008, entitled "Mild Stimulation Device and Measurement Based Design Method for Non-Destructive Control of Complex Rhythmic Systems" the disclosures of which are hereby incorporated by reference herein in their entirety.

GOVERNMENT SUPPORT

Work described herein was supported by Federal Grant No. CTS-0317762 and CBET-0730597, awarded by the National Science Foundation. The Government has certain rights in the invention.

BACKGROUND OF THE INVENTION

Rhythmic patterns and synchronized states are commonly found in complex systems composed of a large number of interacting oscillatory elements. These patterns play a role for a number of biological functions such as cardiac rhythm [1], circadian rhythm [2], olfactory sensation [3], and cognitive processes such as memory and visual perception [4], among others. Conversely, malformed neurological/biological patterns have been linked to diseases such as epilepsy [4], PD-related tremors [5], and cardiac fibrillation [6]. In each of these cases, the emergent behavior of the population is a result of the interactions among individual elements. Early attempts to control the behavior of these oscillatory systems have focused on simply overwhelming the delicate coupling between elements with large external perturbations. Unfortunately, this has the adverse effect of suppressing (or distorting) the natural oscillatory rhythms that comprise the original system. The present invention relates a device and methodology by which a mild perturbation signal can be tailor engineered to produce a desired emergent behavior within a physical or biological oscillatory system. The construction of the signal utilizes the fundamental dynamics which govern oscillatory populations to gently steer the system to the desired state, rather than forcibly driving the system in an un-natural way. The weak nature of the feedback preserves the underlying oscillatory behavior, while controlling the overall emergent behavior of the population. Immediate applications of this methodology include, but are not limited to, the treatment of PD-related tremors, essential tremors, and epileptic seizures.

BRIEF SUMMARY OF INVENTION

A method, system, and computer program product for controlling the behavior of complex rhythmic systems, such as the nervous system, is disclosed. Robust, engineering based measurements of the rhythmic system are taken and used to generate feedback that guides the system towards a desired state. This methodically designed feedback allows the system to maintain the normal behavior of individual elements, thereby achieving high effectiveness, while at the same time minimizing side effects. It therefore becomes possible to move the system towards the desired state in a non-destructive manner. This approach also allows for increased flexibility and applicability because the feedback is generated in a manner that is tailored to the unique variables of the particular system.

In accordance with one or more embodiments, the present invention relates an advanced feedback device and control method which is capable of measuring and regulating/controlling the synchronization properties and spatiotemporal behavior of oscillator populations. The stimulator device can comprise of an external device, which operates outside the target system, or internal device, which operates within the target system, with one or more input electrodes, one or more output electrodes, embedded control logic and memory, power management systems, and one or more external interfaces (e.g. onboard, wired, or wireless). Examples of potential target systems for the present invention include humans, such as a subject or patient, animals, lasers, microwave systems, physical resonators (e.g. any EM system) neurons, chemical oscillators and other naturally occurring and artificial systems.

In accordance with one or more embodiments, the present invention relates the aforementioned nonlinear feedback device which includes a medical drug delivery sub-system for biomedical applications. The delivery system can be activated as a function of the measured synchronization behavior of the system. For example, this could be, but is not limited to, pushing acetylsalicylic acid (aspirin) into the bloodstream at the onset of a myocardial infarction (shown to significantly increase the probability of surviving such an event), or administering anti-seizure medication to augment any active stimulation by the aforementioned device.

In accordance with one or more embodiments, the present invention relates a control method which subtly manipulates the interactions between oscillator elements (via mild perturbations) to control the emergent behavior of the oscillator population. This mild method preserves the physiological (or natural) oscillations of the individual elements in the population.

In accordance with one or more embodiments, the present invention relates a control method for regulating (or eliminating) undesired synchronization in neurological, biological, and/or physical systems while preserving the physiological (or natural) oscillations of the individual elements in the population. This can include, but is not limited to, deep brain electrical stimulation for efficient treatment of neurological disorders such as Parkinson's disease related tremors, epilepsy, and essential tremors, and also cardiac fibrillations.

In accordance with one or more embodiments, the present invention relates a control method for causing synchronization (or synchronization related patterns) in neurological, biological, and/or physical systems while preserving the physiological (or natural) oscillations of the individual elements in the population. This can include, but is not limited to, electrical stimulation for the replacement of pacemaker-like functions, and treatment of cardiac arrhythmias.

In accordance with one or more embodiments, the present invention relates a control method which is derived from the fundamental dynamics of the oscillatory population to be controlled. This allows the control algorithm to be tailored to the specific unique dynamics of the physical system. This can include, but is not limited to, utilizing a phase model representation of the system, constructed from experimental measurements on individual or clusters of oscillating elements.

An aspect of an embodiment of the present invention provides a method of engineering the emergent behavior of a target system having a population of rhythmic elements. The method may comprise: measuring the dynamic properties of the rhythmic elements; using a reduced model to determine the target dynamical behavior of the system; and determining the perturbation that produces the target behavior.

An aspect of an embodiment of the present invention provides an engineering system for engineering the emergent behavior of a target system having a population of rhythmic elements. The engineering system may comprise: a measuring means for measuring the dynamic properties of the rhythmic elements; and a computer processor. The computer processor may be adapted for: using a reduced model to determine the target dynamical behavior of the system; and determining the perturbation that produces the target behavior.

An aspect of an embodiment of the present invention provides a computer program product comprising a computer useable medium having computer program logic for enabling at least one processor in a computer system for engineering the emergent behavior of a target system having a population of rhythmic elements. This engineering of the emergent behavior via of the computer program logic may comprise: receiving data from measuring means for measuring the dynamic properties of the rhythmic elements; using a reduced model to determine the target dynamical behavior of the system, and determining the perturbation that produces the target behavior.

The invention itself, together with further objects and attendant advantages, will best be understood by reference to the following detailed description taken in conjunction with the accompanying drawings.

BRIEF SUMMARY OF THE DRAWINGS

The various embodiments of the present invention comprises a plurality of components and arrangements of components, and a variety of steps and arrangements of steps, embodiments of which are disclosed herein and illustrated in the accompanying drawings, wherein:

FIG. 6: FIG. 6(A) graphically illustrates the effect a mild nonlinear feedback signal, FIG. 6(B), can have on a population of synchronized relaxational oscillators. The feedback was started at ~80 sec and stopped at ~450 sec.

DETAILED DESCRIPTION OF THE INVENTION

Figure 1:
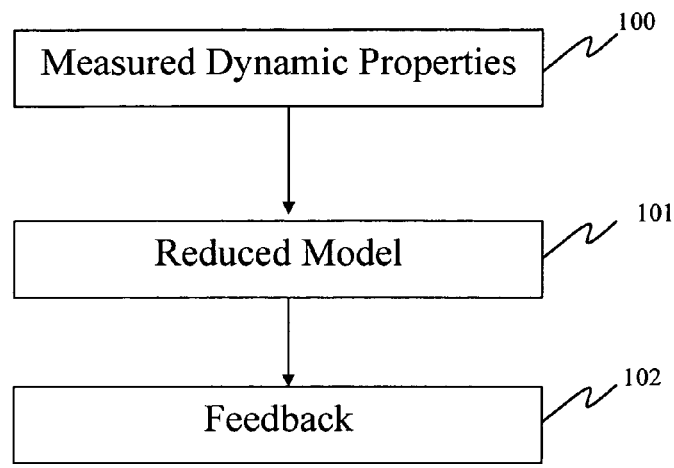
FIG. 1: represents a high-level flow chart of the method approach.

This invention discloses a method of engineering the emergent behavior, illustrated by FIG. 1, of a system having a population of rhythmic elements and comprises measuring the dynamic properties of the rhythmic elements 100, using a reduced model 101 to determine the target dynamical behavior of the system, and determining the perturbation 102 that produces said target behavior. Examples of such emergent behavior include synchronization, desynchronization, phase clustering, propagating waves, multi-cluster states, itinerant clustering, or other spatio-temporal phenomena.

The perturbation could be comprised of feedback, coupling, or forcing, or any combination thereof. The dynamic properties are comprised of the phase behavior of said target system. Measurement of the dynamic properties of the rhythmic elements could be performed through perturbation, for example, using a pulse at every point along a rhythmic element's cycle or using feedback on one or more elements of the population. Measurement could also be performed by measuring the dynamic properties of the rhythmic elements using two or more elements that are desynchronized but interacting and measuring their frequency shift as a function of their phase difference or by using a single oscillator (with, optionally, delayed self-feedback).

The engineering method is performed using an externally, internally, or any combination thereof, relative to the target system. In other words, external performance is performed by external devices and said internal performance is performed by internal devices.

The reduced model comprises at least one of the following phase models: general dynamical models, Kuramoto Phase models, Winfree models, finite pulse models, integrate-and-fire models, and quadratic-integrate-and-fire models, or any combination thereof.

Determining the perturbation comprises taking in a set of individual or aggregated signal measurements in order to construct a feedback loop and can involve pre-processing, processing, and post processing steps. Preprocessing comprises using data filters and smoothing algorithms, said processing comprises using a linear or nonlinear transformation function with adjustable parameters, and post-processing comprises adjusting the output of the processing step to match the conditions of the target system.

Preprocessing can also comprise a nonlinear mathematical transformation, such as a nonlinear mathematical transformation is a time-delayed polynomial. An example of such a polynomial is:

$$f(x) = \frac{K}{N} \sum_{j=1}^{N} \sum_{i=0}^{S} k_i x_j (t - \tau_i)^i$$

where $x_j$ is the $j^{th}$ measured signal at time t such as potential vs. time (EEG/EKG), N is the number of signals measured, S is the feedback order, $k_i$ is the $i^{th}$ polynomial coefficient, $\tau_i$ is the time-delay of the $i^{th}$ polynomial term, and K is the overall gain. Finally, the feedback loop can comprise one or more signals that are applied in either a uniform or non-uniform manor to the targeted area of the population.

The rhythmic elements can be comprised of oscillators, such as electrochemical oscillators, general chemical oscillators, pH oscillators, Coherent EM sources or sinks (such as lasers or microwave sources.), self-sustaining physical resonators, radio antenna arrays, electron spin, neurons, general biological cells (protein and gene expression within such cells), cardiac muscle, or any combination or grouping thereof. The oscillators can also be comprised of a number of individual oscillators, such as a neural cluster (i.e. a group of individual neurons). The oscillators can also comprise elements that undergo periodic or aperiodic fluctuations of physical quantities (for example, brain waves, laser elements, microwave elements, electrochemical elements, neurons, and cardiac muscle).

The rhythmic elements can also be components of rhythmic systems that are involved the collective behavior of the target system, such as circadian rhythms, olfactory sensations, cardiac fibrillation, and cognitive processes (processes comprise those related to memory and visual perception), and tremors (Parkinson's disease-related tremors, epileptic seizures, and essential tremors).

Figure 2:
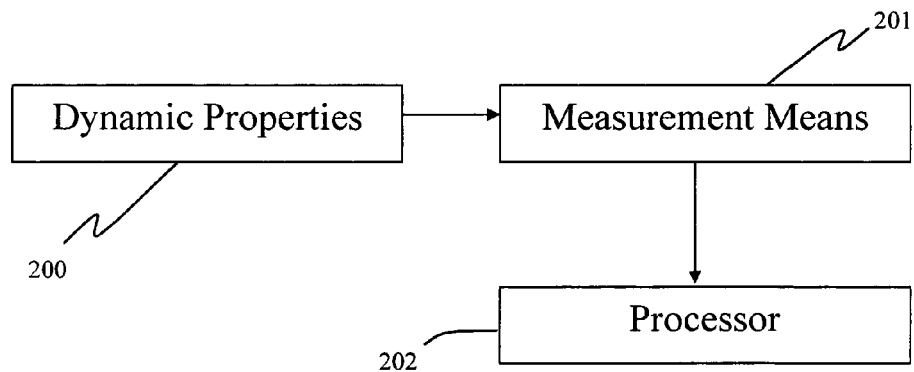
FIG. 2: represents a schematic block diagram of the system approach.

This invention also discloses a system for engineering the emergent behavior, illustrated by FIG. 2, of a target system having a population of rhythmic elements and comprises a measuring means 201 for measuring the dynamic properties of the rhythmic elements 200 and a computer processor 202 that is adapted for using a reduced model to determine the target dynamical behavior of the system and for determining the perturbation that produces said target behavior. The computer processor could be either an ASIC processor or FPGA. The measuring means can comprise optical sensors, voltage meters, current meters, pH meters, EEG, EKG, MEG, Ohm meters, magnetic flux meters, electric field meters, thermometers, patch clamps, neural electrodes, electrode arrays, or any combination thereof.

Examples of emergent behavior include synchronization, desynchronization, phase clustering, propagating waves, multi-cluster states, itinerant clustering, or other spatio-temporal phenomena.

The perturbation could be comprised of feedback, coupling, or forcing, or any combination thereof. The dynamic properties are comprised of the phase behavior of said target system. Measurement of the dynamic properties of the rhythmic elements could be performed through perturbation, for example, using a pulse at every point along a rhythmic element's cycle or using feedback on one or more elements of the population. Measurement could also be performed by measuring the dynamic properties of the rhythmic elements using two or more elements that are desynchronized but interacting and measuring their frequency shift as a function of their phase difference or by using a single oscillator (with, optionally, delayed self-feedback).

The system is can used externally, internally, or any combination thereof, relative to the target system. In other words, external performance is performed by external devices and said internal performance is performed by internal devices. Such devices are comprised of one or more input electrodes, one or more output electrodes, embedded control logic and memory, power management systems, and one or more external interfaces (onboard interfaces, wired interfaces, or wireless interfaces).

The reduced model comprises at least one of the following phase models: general dynamical models, Kuramoto Phase models, Winfree models, finite pulse models, integrate-and-fire models, and quadratic-integrate-and-fire models, or any combination thereof.

Determining the perturbation comprises taking in a set of individual or aggregated signal measurements in order to construct a feedback loop and can involve pre-processing, processing, and post processing steps. Preprocessing comprises using data filters and smoothing algorithms, said processing comprises using a linear or nonlinear transformation function with adjustable parameters, and post-processing comprises adjusting the output of the processing step to match the conditions of the target system.

Preprocessing can also comprise a nonlinear mathematical transformation, such as a nonlinear mathematical transformation is a time-delayed polynomial. An example of such a polynomial is:

$$f(x) = \frac{K}{N} \sum_{j=1}^{N} \sum_{i=0}^{S} k_i x_j (t - \tau_i)^i$$

where $x_j$ is the $j^{th}$ measured signal at time t such as potential vs. time (EEG/EKG), N is the number of signals measured, S is the feedback order, $k_i$ is the $i^{th}$ polynomial coefficient, $\tau_i$ is the time-delay of the $i^{th}$ polynomial term, and K is the overall gain. Finally, the feedback loop can comprise one or more signals that are applied in either a uniform or non-uniform manor to the targeted area of the population.

The rhythmic elements can be comprised of oscillators, such as electrochemical oscillators, general chemical oscillators, pH oscillators, Coherent EM sources or sinks (such as lasers or microwave sources.), self-sustaining physical resonators, radio antenna arrays, electron spin, neurons, general biological cells (protein and gene expression within such cells), cardiac muscle, or any combination or grouping thereof. The oscillators can also be comprised of a number of individual oscillators, such as a neural cluster (i.e. a group of individual neurons). The oscillators can also comprise elements that undergo periodic or aperiodic fluctuations of physical quantities (for example, brain waves, laser elements, microwave elements, electrochemical elements, neurons, and cardiac muscle).

The rhythmic elements can also be components of rhythmic systems that are involved the collective behavior of the target system, such as circadian rhythms, olfactory sensations, cardiac fibrillation, and cognitive processes (processes comprise those related to memory and visual perception), and tremors (Parkinson's disease-related tremors, epileptic seizures, and essential tremors).

This invention is not limited in its application to the details of construction and the arrangement of components set forth in the following description of illustrated in the drawings. The invention is capable of other embodiments and of being practiced or of being carried out in various ways. Also the phraseology and terminology used herein is for the purpose of description, and should not be regarded as limiting. The use of "including," "comprising," "having," "containing," "involving," and variations therein, is meant to encompass the items listed thereafter and equivalents thereof as well as additional items. The examples presented are for illustrative purposes only, and should not be considered limiting to the scope of the invention.

Figure 3:
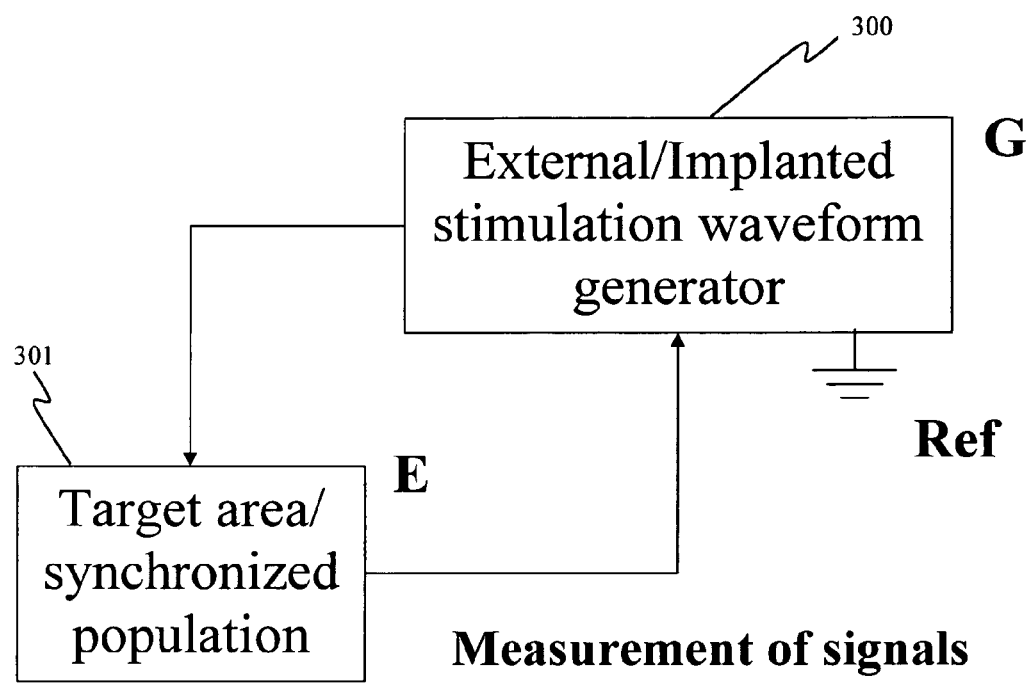
FIG. 3: diagrammatically illustrates a nonlinear feedback stimulation waveform generator according to an embodiment of the present invention.
Figure 4:
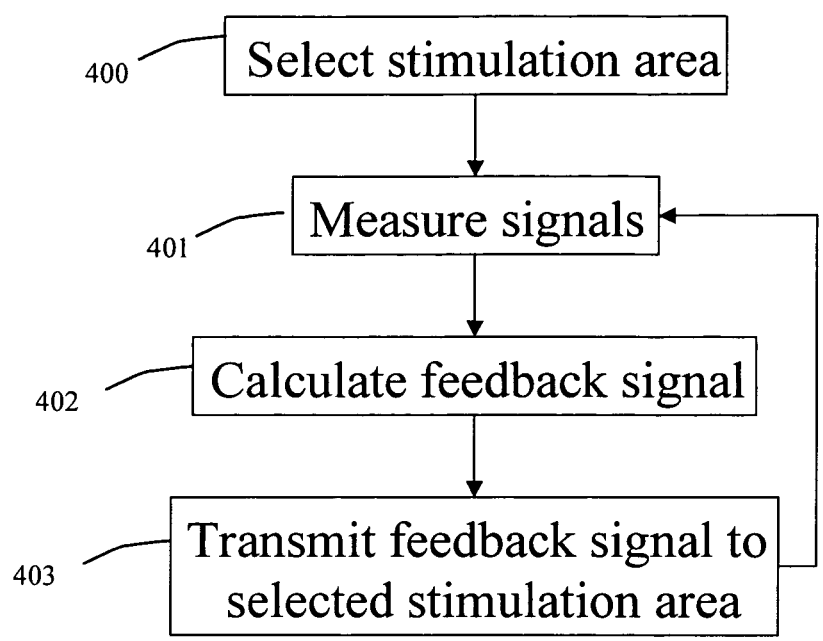
FIG. 4: is a flowchart that illustrates the feedback stimulation method according to an embodiment of the present invention.

A feedback waveform generator 300 is illustrated in FIG. 3. The hardware of the generator 300 may be conventional and can be external to the stimulated system. The generator 300 is used to produce a signal which perturbs the target area (shown as "Target area/synchronized population", in FIG. 3), causing a change in the behavior of the population. However, unlike known stimulation generators, the feedback waveform generator 300 is configured or programmed to output novel and unobvious stimulation waveforms in accordance with the various embodiments of the present invention. The same conventional hardware 301, or a separate hardware in appropriate locations, can be used to obtain measurements of the targeted area, which are used as inputs to the feedback waveform generator 300. In the application of deep brain stimulation, 301 can be considered to be a conventional electrode, such as a metal microelectrode or a multiple-contact electrode, which is inserted into the desired location in the brain A method for generating and applying the feedback signal in accordance with an embodiment of the present invention using the generator 300 in FIG. 3 is disclosed in FIG. 4. A feedback loop is constructed in which a set of individual or aggregated signals 400 is measured 401, and fed into a processor device 402. This device preprocesses the data (if necessary) to reduce any noise from the measurement, and performs a nonlinear mathematical transformation on this set of signals. A simple example of the functional form of this transformation is, but is not limited to, a time-delayed polynomial of the form:

$$f(x) = \frac{K}{N}\sum_{j=1}^{N}\sum_{i=0}^{S} k_i x_j (t - \tau_i)^i$$

where $x_j$ is the $j^{th}$ measured signal at time t such as potential vs. time (EEG/EKG), N is the number of signals measured, S is the feedback order, $k_i$ is the $i^{th}$ polynomial coefficient, $\tau_i$ is the time-delay of the $i^{th}$ polynomial term, and K is the overall gain. The output of this transformation 403 can be one or more signals which are applied in either a uniform or non-uniform manor to the targeted area of the population. The feedback signal causes a slight shift in the frequency and amplitude of the oscillating element. This new state is then re-measured 401, and the process is repeated.

Figure 5:
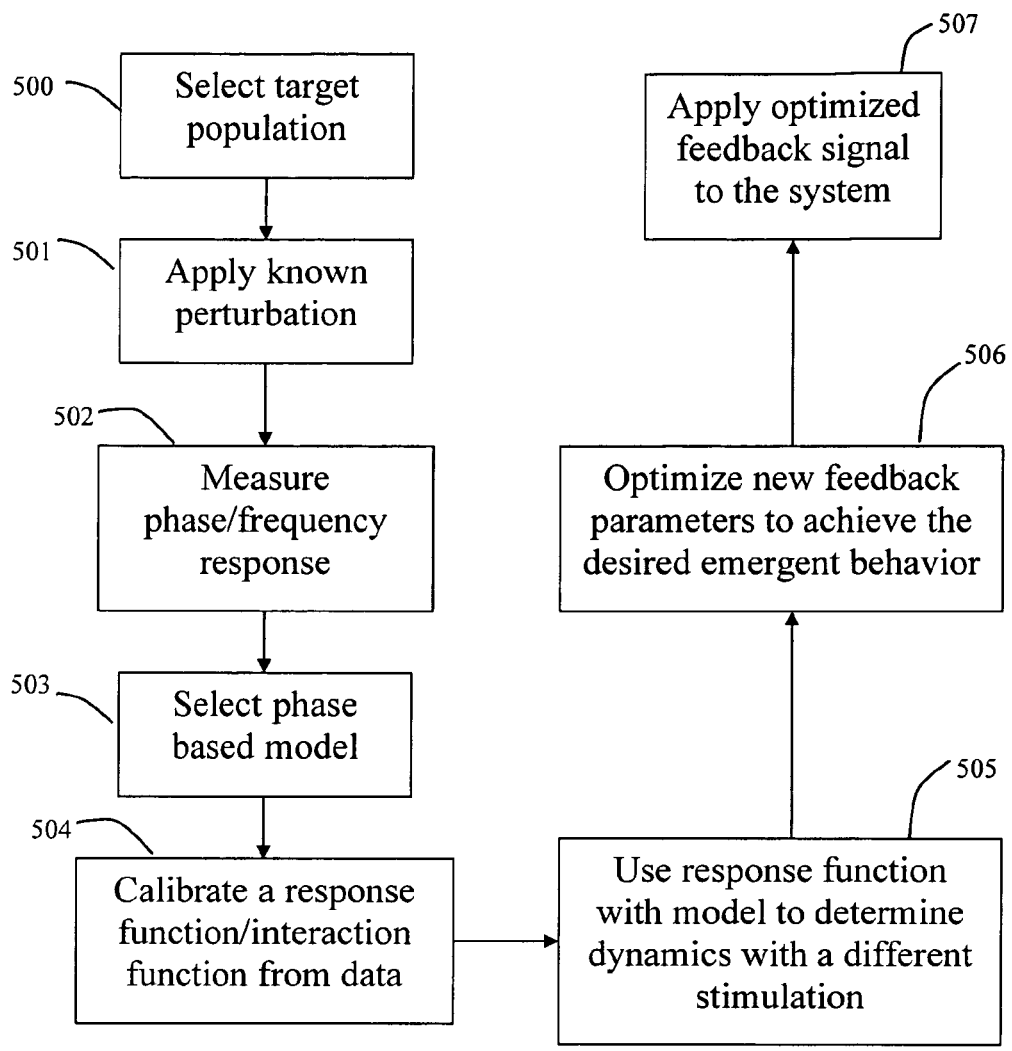
FIG. 5: is a flowchart that illustrates the method by which the parameters of the feedback function can be determined to achieve a desired neural dynamical behavior.

A method for obtaining the shape of the feedback function in accordance with an embodiment of the present invention using the generator 300 in FIG. 3 is disclosed in FIG. 5. As previously stated, a mild perturbation to an oscillator causes a slight shift in its phase. However, the magnitude (as well as direction) of this phase advance is a function the phase at which the oscillator is perturbed. In other words, the limit cycle has a non-uniform sensitivity to perturbations, and thus some phases are more sensitive to perturbations then others. The function that represents the magnitude of the phase advance (or delay) of an oscillator as a function of the phase at which it is perturbed is defined as a response function. The response function is an intrinsic property of the oscillator(s) of interest, and can be experimentally measured (directly or indirectly) from a single oscillating element, multiple elements, or a population of elements. [12,13] To obtain a response function, a target area 500 is selected which contains the element(s) to be measured. The area is stimulated 501 (an example could be, but is not limited to, a pulse train, or a known feedback signal), resulting in a slight change in the oscillator's frequency. This stimulation is repeated at each point along the limit cycle of the oscillator(s). The stimulation response data 502 are then used to determine the response function in conjunction with an appropriate model 503, which could include, but is not limited to, a phase based model such as a Kuramoto or Winfree model or a finite pulse models such as seen in the work of Izhikevich [14]. Once the response function is obtained 504, it can be applied to the phase model to extrapolate the behavior of the population under various stimulation conditions 505. However, this process can be reversed to determine a feedback waveform which will produce the desired behavior. To accomplish this, a phase model must first be constructed which reproduces the desired state. Applying the measured response function to this target model, gives a system with only one free parameter, the feedback waveform. A numerical optimization is then used to calculate the feedback waveform which will produce the desired state 506, which can then be applied to the target system 507. Therefore, this method allows a specific emergent behavior to be directly engineered into the targeted population, without any knowledge of the underlying chemical, electrical, or biological mechanisms. These behaviors can include but are not limited to synchronization, desynchronization, phase clustering, propagating waves, and other spatiotemporal patterns, depending on the specific effect to be achieved. Since the response function is a measured property of the oscillator(s) to be manipulated, the resulting model (and subsequent feedback signal) is calibrated to the specific behavior of the original system by design. In a neurobiological application, this is equivalent to a personalized medical treatment which accounts for patient-specific neuropathy. Examples of the application of this methodology can be found in [13].

Patents for implantable devices/subsystems (including methods) for the detection and control of neurological disorders (epilepsy, Parkinson's tremors and migraine headaches) and using window based predictor/corrector methods (such as slope, integral, correlations of EEG waveform measurements) have been issued to Neuropace, Inc. (U.S. Pat. Nos. 6,810,285, 6,647,296, 6,529,774, 6,480,743, 6,466,822, 6,459,936, 6,353,754, 6,134,474, 6,128,538, 6,061,593, 6,016,449, etc., of which are incorporated by reference herein.)

Patents for implantable devices/subsystems (including methods) for the detection and control of neurological and cardiovascular disorders (epilepsy, Parkinson's tremors and migraine headaches, myocardial infarction, cardiac fibrillations, and cardiac arrhythmias) using phase shift, pulsing, and other empirical methods have been issued to Medtronic, Inc. (U.S. Pat. Nos. 7,096,064, 7,149,572, 5,129,393, etc., of which are incorporated by reference herein.)

Methods for controlling the spatiotemporal behavior of oscillator populations have been shown in the work of Hudson et al. [7,8], Tass [9,10] and Pikovsky et al. [11]

Figure 9:
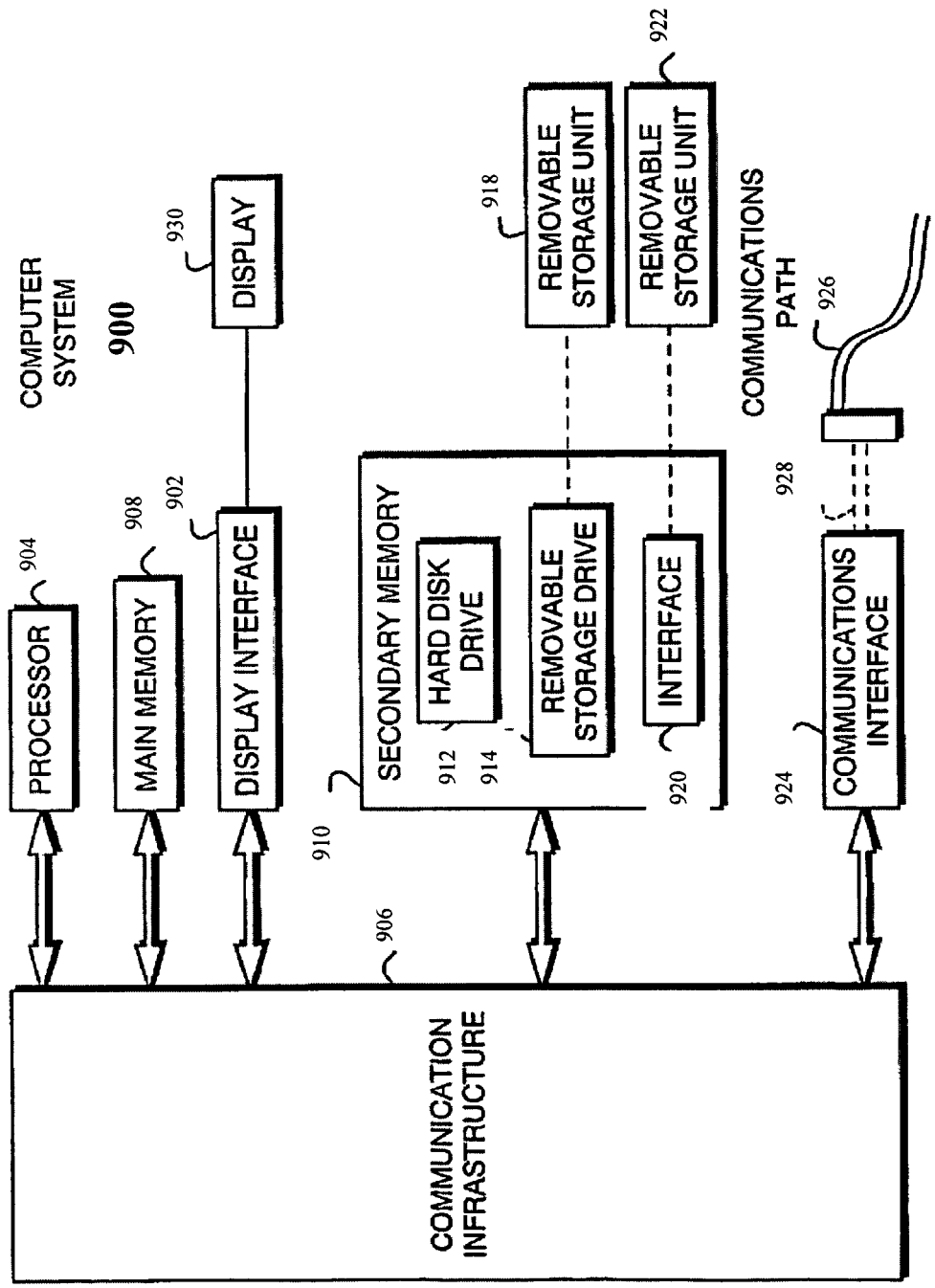
FIG. 9 is a functional block diagram for a computer system for implementation of an exemplary embodiment or portion of an embodiment of present invention.

Turning to FIG. 9, FIG. 9 is a functional block diagram for a computer system 800 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 900 as illustrated in FIG. 9. The computer system 800 may includes one or more processors, such as processor 904. The Processor 904 is connected to a communication infrastructure 906 (e.g., a communications bus, cross-over bar, or network). The computer system 900 may include a display interface 902 that forwards graphics, text, and/or other data from the communication infrastructure 906 (or from a frame buffer not shown) for display on the display unit 930. Display unit 830 may be digital and/or analog.

The computer system 900 may also include a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, a flash memory, etc. The removable storage drive 914 reads from and/or writes to a removable storage unit 918 in a well known manner. Removable storage unit 918, represents a floppy disk, magnetic tape, optical disk, etc. which is read by and written to by removable storage drive 914. As will be appreciated, the removable storage unit 918 includes a computer usable storage medium having stored therein computer software and/or data.

In alternative embodiments, secondary memory 910 may include other means for allowing computer programs or other instructions to be loaded into computer system 900. Such means may include, for example, a removable storage unit 922 and an interface 820. Examples of such removable storage units/interfaces include a program cartridge and cartridge interface (such as that found in video game devices), a removable memory chip (such as a ROM, PROM, EPROM or EEPROM) and associated socket, and other removable storage units 922 and interfaces 920 which allow software and data to be transferred from the removable storage unit 922 to computer system 900.

The computer system 900 may also include a communications interface 924. Communications interface 924 allows software and data to be transferred between computer system 900 and external devices. Examples of communications interface 924 may include a modem, a network interface (such as an Ethernet card), a communications port (e.g., serial or parallel, etc.), a PCMCIA slot and card, a modem, etc. Software and data transferred via communications interface 924 are in the form of signals 928 which may be electronic, electromagnetic, optical or other signals capable of being received by communications interface 924. Signals 928 are provided to communications interface 924 via a communications path (i.e., channel) 926. Channel 926 (or any other communication means or channel disclosed herein) carries signals 928 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 914, a hard disk installed in hard disk drive 912, and signals 928. These computer program products ("computer program medium" and "computer usable medium") are means for providing software to computer system 900. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 908 and/or secondary memory 910. Computer programs may also be received via communications interface 924. Such computer programs, when executed, enable computer system 900 to perform the features of the present invention as discussed herein. In particular, the computer programs, when executed, enable processor 904 to perform the functions of the present invention. Accordingly, such computer programs represent controllers of computer system 900.

In an embodiment where the invention is implemented using software, the software may be stored in a computer program product and loaded into computer system 800 using removable storage drive 914, hard drive 912 or communications interface 924. The control logic (software or computer program logic), when executed by the processor 904, causes the processor 904 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

EXAMPLES

Practice of the invention will be still more fully understood from the following examples, which are presented herein for illustration only and should not be construed as limiting the invention in any way.

Example 1

Figures 7A, 7B, 7C:
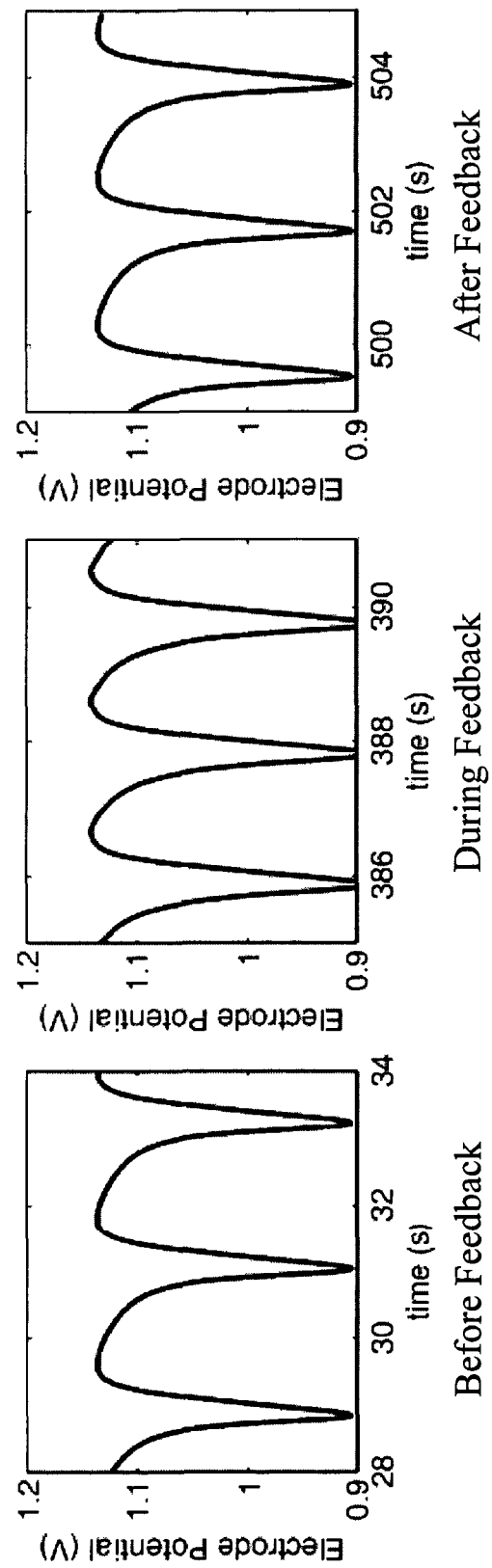
FIG. 7: graphically illustrates a single representative element of the population before (FIG. 7(A)), during (FIG. 7(B)), and after (FIG. 7(C)) the application of feedback illustrated in FIG. 6(B).
Figure 8:
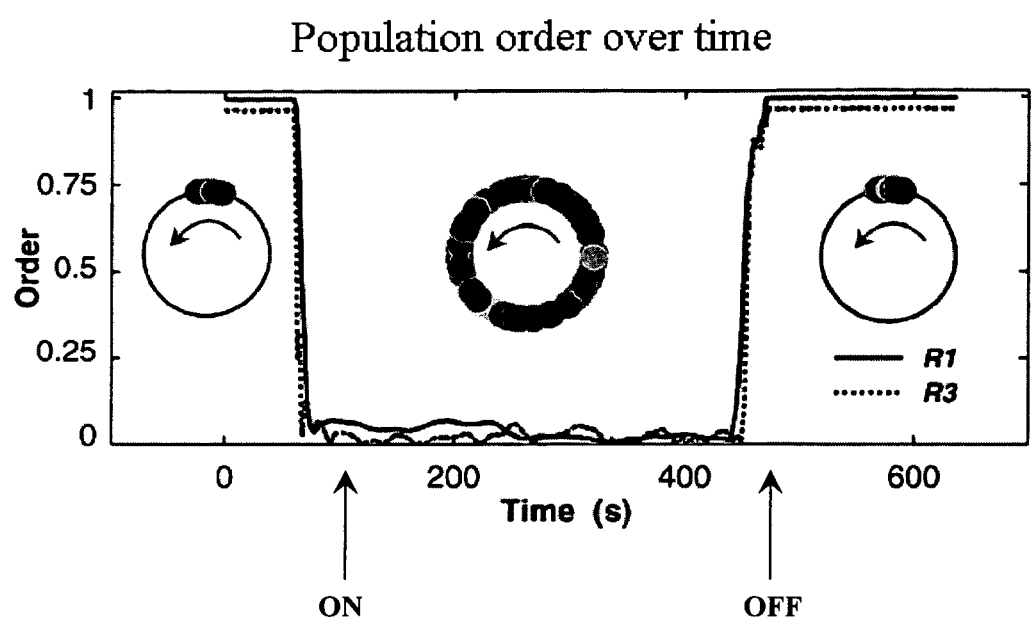
FIG. 8: graphically depicts the order of the relaxational population in FIG. 6(A) over time. The phase loops illustrate the relative phase of each oscillator in the population.

In the embodiment of a population of synchronized nonlinear electrochemical oscillators, second order polynomial feedback is required to stabilize the desynchronized state. FIG. 6(A) graphically illustrates the collective signal of a cluster of 64 electrochemical oscillators before, during and after the application of nonlinear feedback, FIG. 6(B) in accordance with the method disclosed in FIG. 4. It can be seen that the amplitude of the collective signal (the extent of desynchronization) substantially decreased with the application of designed nonlinear feedback. The feedback was started at ~80 sec and stopped at ~450 sec. The collective oscillation signal shown here is simply the sum of all individual oscillator elements in the population, normalized by the size of the population. FIG. 8 graphically demonstrates how the order of the system (a robust measurement of synchronization where 1 is complete synchronization and 0 is complete desynchronization) changes over time with the application of nonlinear feedback in accordance with some embodiments of the disclosure. The relative phases of each oscillating element are shown in the circles accompanying the figure. This suppression of synchrony can be maintained indefinitely so long as the integrity of the feedback signal is preserved. FIGS. 7(A-C) graphically illustrate the non-destructive effect the feedback has on the waveform of the oscillations before, during, and after application of the feedback, respectively. The individual elements of the population oscillate with an amplitude of approximately 250 mV. The amplitude of the feedback signal is approximately 10 mV, a factor of 25 smaller than the amplitude of a single element. This mild feedback ensures that the shape of the oscillator waveform remains undisturbed under feedback conditions.

Example 2

It has been found that PD-related tremor and essential tremor are caused by pathological synchronous firing of clusters of neurons [15-17]. Currently, an effective therapy called deep brain stimulus is performed by administering a permanent high-frequency (HF) (>100 Hz) periodic pulse train via electrodes (leads) implanted in the defined target in the brain. However, during high frequency DBS, the individual neuronal firing is unphysiologically suppressed [18]. This results in the adaptation of the stimulated neuronal networks and usually requires an increases in the amplitude of the stimulation during the treatment, and the spread of the stronger currents may lead to severe side effects.

Present "primitive" pulse stimulators are designed based on empirical rules and simple pulse forms that limit their applicability. Instead of simply suppressing the neuronal firing in the pacemaker-like cluster, this novel stimulation technique aims to desynchronize the pacemaker's pathologically synchronized firing in a demand-controlled way. A nonlinear feedback signal, in accordance with some embodiments of the invention, can be determined using a phase model based approach. Since this multi-scale model utilizes experimental measurements of the response function of the individual oscillatory elements, it can account for the unique characteristics of the patients neurophysiology in a methodical manor. This can include medically relevant properties of biological rhythms such as changes in amplitude, transient dynamics, heterogeneities, inherent noise and drift. A mild feedback signal can be constructed, in accordance with some embodiments of the invention, which can generate one of many spatiotemporal phenomenon including, but not limited to, synchronization, desynchronization, pacemaker and anti-pacemaker synchronization, phase cluster formation, spatial clusters, itinerant clustering, and propagating waves.

The mild nature of the feedback allows the oscillatory behavior of all the individual elements to be maintained during the application of a desynchronizing signal, bringing the system close to its physiological mode. [13]

Compared with other methods of desynchronization, such as localized stimulation of neural sub-populations and large amplitude pulsed stimulations, the nonlinear feedback stimulation actively maintains the desynchronized state, instead of simply shocking the effected area and waiting for the onset of re-synchronization. The proposed method represents a more physiologically accurate approach compared to the current empirical methodology commonly used in conventional HFDBS. In addition, the mild feedback stimulation can decrease the energy consumption, dramatically improve the battery performance beyond that of present day devices.

In summary, the various embodiments of the present invention provide, but are not limited to, new nonlinear feedback and control techniques that can offer approaches to engineering the dynamics of oscillatory populations. These techniques rely upon a phase model approach which is calibrated using experimental measurements of the oscillatory system. These measurements ensure that the model captures the fundamental dynamics of the system, and allows the non-trivial feedback signals to be customized to account for the unique properties of the targeted system. Applications can include improving current neurological stimulation treatments which aim to suppress pathological, synchronized cerebral activity such as in Parkinson's disease, essential tremor, and epilepsy. From the results of the embodiment of electrochemical oscillator populations, the mild nature of the nonlinear feedback stimulation has been shown to preserve the normal oscillations of all individual elements during the application of feedback. Thus the system can be gently steered towards the desired state (synchronization, desynchronization, clustering, etc.) while maintaining the natural mode of the individual oscillatory elements. In neurological systems, this methodology provides a more accurate physiological representation of the synchronization dynamics of the system when compared to current devices and methodologies which utilize empirical rules and large magnitude stimulations, which unnaturally suppress neuronal firing.

ADDITIONAL REFERENCES

The following patents, applications and publications as listed below are hereby incorporated by reference in their entirety herein. Moreover, the devices, systems, compositions, and computer program products and methods of various embodiments of the present invention disclosed herein may utilize aspects disclosed in the following U.S. patents, foreign patents, and publications.

P. Tass (1999) Phase Resetting in Medicine and Biology. Stochastic Modeling and Data Analysis.

Peter A. Tass, Synergistics of the Nervous System: from Basic Principles to Therapy. Nonl. Phen. Compl. Syst. 5 (4), 470-478. (2002).

P. A. Tass (2003). "A model of desynchronization deep brain stimulation with a demand-controlled coordinated reset of neural subpopulations." Biological Cybernetics 89 (2): 81-88.

Tass, P. A. Patent WO 03/077985 A1. "Device for treating patients by means of Brain stimulation."

Tass, P. A. Patent WO 03/077985 A1. "Device for modulation of neuronal activity in the brain by means of sensory stimulation and detection of brain activity."

Oleksandr V. Popovych, Christian Hauptmann, and Peter A. Tass, "Effective Desynchronization by Nonlinear Delayed Feedback", Phys. Rev. Lett. 94, 164102 (2005).

Oleksandr V. Popovych•Christian Hauptmann, Peter A. Tass, "Control of neuronal synchrony by nonlinear delayed feedback" Biol. Cybern. 95: 69-85 (2006).

U.S. Pat. No. 7,209,787 B2 to DiLorenzo, entitled "Apparatus and Method for Closed-Loop Intracranial Stimulation for Optimal Control of Neurological Disease", Apr. 24, 2007

U.S. Patent Application Publication No. 2005/0124848 A1 to Holzner, entitled "Method and Apparatus for Electromagnetic Modification of Brain Activity", Jun. 9, 2005.

U.S. Pat. No. 7,146,218 B2 to Esteller, et. al., entitled "Adaptive Method and Apparatus for Forecasting and Controlling Neurological Disturbances Under a Multi-Level Control.

In summary, an aspect of the present invention provides methodology which allows the emergent behavior of a population of rhythmic elements to be engineered to achieve a specific desirable state. This method has been successfully used to engineer an experimental system of chemical oscillators to exhibit emergent behaviors such as synchronization, desynchronization, multi-cluster states, and itinerant clustering using a mild feedback signal. Controlling such behaviors is an important issue in physical and biological systems such as laser and microwave devices, cardiac pacemakers and neurological stimulation devices.

For biomedical applications, the new feedback technique, designed for desynchronizing neuronal clusters, can be a promising approach to improve neurological stimulation techniques aimed at suppressing pathological, synchronized cerebral activity such as in Parkinson's disease, essential tremor, or epilepsy. Conventional high frequency deep brain stimulation (HFDBS) relies on simple empirical rules (which do not account for the underlying dynamics of the system)

and strongly alters the dynamics of the affected populations, e.g., by blocking neuronal firing. Over time the treatment becomes less effective, requiring a larger magnitude stimulation to achieve the same level of therapeutic benefit. This novel approach utilizes a feedback stimulation which is tailored to the unique properties of the system via a simple yet robust measurement based engineering method. This allows the system to achieve a high effectiveness while minimizing the magnitude of the stimulation, circumventing many of the current side effects of conventional HFDBS. The methodically designed feedback allows the system to maintain the normal oscillations of all individual elements during desynchronization. Hence the dynamics of the system will be brought close to its physiological mode, without occurrence of pathological synchronization.

This novel approach to engineering dynamical systems overcomes the limitations of conventional HFDBS by increasing the therapeutic benefit and through minimizing undesirable side effects. The feedback design method can be used to customize the stimulation for the unique physiological properties of each patient, while its mild nature decreases side effects while improving battery performance.

Various embodiments of the present invention may be utilized for, but not limited thereto, products and services such as Deep Brain Stimulators for treatment of essential tremor, treatment of Parkinson's disease related tremors, treatment of epileptic seizures as well as cardiac pacemakers that feature improved efficiency and effectiveness.

Some exemplary biomedical application related advantages associated with the various embodiments of the present invention may include, but are limited to, mild feedback, improved effectiveness, and patient specific therapy. Since the method requires a mild global feedback signal to be effective, the side effects of current large magnitude HFDBS can be avoided, which also improves battery lifetime. In addition, current HFDBS uses empirical rules to achieve results. This novel feedback utilizes a more physiologically and dynamically accurate model of complex systems. Finally, this method can utilize patient specific physiological data to custom engineer the most effective stimulation waveform to achieve the desired effect for each individual patient.

END NOTE REFERENCES

The following patents, applications and publications as listed below and throughout this document are hereby incorporated by reference in their entirety herein. Moreover, the devices, systems, compositions, and computer program products and methods of various embodiments of the present invention disclosed herein may utilize aspects disclosed in the following U.S. patents, foreign patents, and publications:

1) D. J. Christini, L. Glass, *Chaos* 12, 732 (2002).
2) S. M. Reppert, D. R. Weaver, *Nature* 418, 935 (2002).
3) G. Laurent, *Nature Rev. Neuro.* 3, 884 (2002).
4) P. J. Uhhaas, W. Singer, *Neuron* 52, 155 (2006).
5) P. A. Tass, *Phase Resetting in Medicine and Biology. Stochastic Modeling and Data Analysis* (Springer, Berlin, 1999).
6) M. A. Allessie, F. I. M. Bonke, F. J. G. Schopman, *Circulation Res.* 41, 1 (1977).
7) Y. Zhai, I. Z. Kiss, and J. L. Hudson, Ind. *Eng. Chem. Res.* 43, 315 (2004).
8) I. Z. Kiss, Y. Zhai, J. L. Hudson, *Science,* 296, 1676 (2002).
9) O. V. Popovych, C. Hauptmann, P. A. Tass, *Phys. Rev. Lett.* 94, 164102 (2005).
10) O. V. Popovych, C. Hauptmann, P A. Tass, *Biol. Cybern.* 95, 69-85 (2006)
11) M. Rosenblum, N. Tukhlina and A. Pikovsky, *Int. J. Bif. Chaos* 16, 7 (2006).
12) I. Z. Kiss, Y. Zhai, J. L. Hudson, *Phys. Rev. Lett.* 94, 248301 (2005).
13) I. Z. Kiss, C. G. Rusin, H. Kori, J. L. Hudson, *Science. In press* (2007).
14) E. M. Izhikevich, *IEEE Trans. Neural Networks* 10, 499 (May, 1999).
15) R. Llinas, H. Jahnsen, *Nature* 297, 5865, 406-408 (1982).
16) J. Volkmann, M. Joliot, et al. *Neurology* 46, 5, 1359-1370 (1996).
17) R. J Elble, and W. C. Koller. *Tremor*. Baltimore, Johns Hopkins University Press (1990).
18) C. C. McIntyre, M. Savasta, et al. *Clinical Neurophysiology* 115, 6, 1239-1248 (2004).

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A method of engineering emergent behavior of a target system having a population of rhythmic elements, comprising:
measuring dynamic properties of the rhythmic elements;
using a reduced model to determine target dynamical behavior of the target system;
determining perturbation that produces said target behavior; and wherein:
said perturbation comprises taking in a set of individual or aggregated signal measurements in order to construct a feedback loop,
said determining said feedback loop comprises at least one of pre-processing, processing, and post processing steps, and
said determining said preprocessing comprises using data filters and smoothing algorithms, said processing comprises using a linear or nonlinear transformation function with adjustable parameters, and said post-processing comprises adjusting the output of the processing step to match the conditions of the target system.

2. The method of claim 1, wherein said perturbation comprises feedback, coupling, or forcing, or any combination thereof.

3. The method of claim 1, wherein said dynamic properties are comprised of the phase behavior of said target system.

4. The method of claim 1, wherein said emergent behavior may comprise, but is not limited to, the following behaviors: synchronization, desynchronization, phase clustering, propagating waves, multi-cluster states, itinerant clustering, or other spatio-temporal phenomena.

5. The method of claim 1, wherein said measuring of the dynamic properties of the rhythmic elements could be performed through perturbation.

6. The method of claim 5, wherein said perturbation comprises using a pulse at every point along a rhythmic element's cycle.

7. The method of claim 5, wherein said perturbation comprises using feedback on one or more elements of the population.

8. The method of claim 1, wherein said measuring the dynamic properties of the rhythmic elements could be performed using two or more elements that are desynchronized but interacting and measuring their frequency shift as a function of their phase difference.

9. The method of claim 1, wherein said measuring the dynamic properties of the rhythmic elements could be performed using a single oscillator.

10. The method of claim 9, wherein said oscillator is used with delayed self-feedback.

11. The method of claim 1, wherein said engineering method is performed externally, internally, or any combination thereof, relative to the target system.

12. The method of claim 11, wherein said external performance is performed by external devices and said internal performance is performed by internal devices.

13. The method of claim 1, wherein said reduced model comprises at least one of the following phase models: general dynamical models, Kuramoto Phase models, Winfree models, finite pulse models, integrate-and-fire models, and quadratic-integrate-and-fire models, or any combination thereof.

14. The method of claim 1, where said preprocessing comprises a nonlinear mathematical transformation.

15. The method of claim 14, where said nonlinear mathematical transformation is a time-delayed polynomial.

16. The method of claim 15, wherein said time-delayed polynomial is of the form $$f(x) = \frac{K}{N} \sum_{j=1}^{N} \sum_{i=0}^{S} k_i x_j (t - \tau_i)^i$$

where $x_j$ is the $j^{th}$ measured signal at time t such as potential vs. time (EEG/EKG), N is the number of signals measured, S is the feedback order, $k_i$ is the $i^{th}$ polynomial coefficient, $\tau_i$ is the time-delay of the $i^{th}$ polynomial term, and K is the overall gain.

17. The method of claim 1, where said feedback loop comprises one or more signals that are applied in either a uniform or non-uniform manor to the targeted area of the population.

18. The method of claim 1, wherein said rhythmic elements comprises oscillators.

19. The method of claim 18, wherein said oscillators comprise at least one of the following: electrochemical oscillators, general chemical oscillators, pH oscillators, Coherent EM sources or sinks, self-sustaining physical resonators, radio antenna arrays, electron spin, neurons, general biological cells, cardiac muscle, or any combination or grouping thereof.

20. The method of claim 19, wherein said Coherent EM sources or sinks comprise lasers or microwave sources.

21. The method of claim 19, wherein said general biological cells comprise protein and gene expression within those cells.

22. The method of claim 19, wherein said oscillators comprise a number of individual oscillators.

23. The method of claim 22, wherein said individual oscillators comprise a neural cluster (i.e. a group of individual neurons).

24. The method of claim 18, wherein said oscillators comprise, but are not limited to, elements which undergo periodic or aperiodic fluctuations of physical quantities.

25. The method of claim 24, wherein said fluctuations of physical quantities comprise those found in: brain waves, laser elements, microwave elements, electrochemical elements, neurons, and cardiac muscle.

26. The method of claim 1, wherein said rhythmic elements are components of rhythmic systems.

27. The method of claim 26, wherein said rhythmic systems comprise those involved in the collective behavior of the target system.

28. The method of claim 27, wherein said collective behavior comprises at least one of the following: circadian rhythms, olfactory sensations, cardiac fibrillation, and cognitive processes, and tremors.

29. The method of claim 28, where said cognitive processes comprise those related to memory and visual perception.

30. The method of claim 28, where said tremors comprise Parkinson's disease-related tremors, epileptic seizures, and essential tremors.

31. The system of claim 1, wherein said time-delayed polynomial is of the form $$f(x) = \frac{K}{N}\sum_{j=1}^{N}\sum_{i=0}^{S}k_i x_j(t-\tau_i)^i$$

where $x_j$ is the $j^{th}$ measured signal at time t such as potential vs. time (EEG/EKG), N is the number of signals measured, S is the feedback order, $k_i$ is the $i^{th}$ polynomial coefficient, $\tau_i$ is the time-delay of the $i^{th}$ polynomial term, and K is the overall gain.

32. The system of claim 1, where said feedback loop comprises one or more signals that are applied, in either a uniform or non-uniform manor to the targeted area of the population.

33. An engineering system for engineering emergent behavior of a target system having a population of rhythmic elements, comprising:
  a measuring means for measuring dynamic properties of the rhythmic elements;
  a computer processor, wherein said computer processor is adapted for:
    using a reduced model to determine target dynamical behavior of the system,
    determining perturbation that produces said target behavior, and wherein:
      said feedback comprises taking in a set of individual or aggregated signal measurements in order to construct a feedback loop,
      said determining said feedback further comprises preprocessing said taken in set of individual or aggregated signal measurements if necessary for the construction of said feedback,
      said preprocessing comprises a nonlinear mathematical transformation, and
      said nonlinear mathematical transformation is a time-delayed polynomial.

34. The engineering system of claim 33, wherein said processor comprises either an ASIC processor or FPGA.

35. The engineering system of claim 33, wherein said measuring means comprises optical sensors, voltage meters, current meters, pH meters, EEG, EKG, MEG, Ohm meters, magnetic flux meters, electric field meters, thermometers, patch clamps, neural electrodes, electrode arrays, or any combination thereof.

36. The engineering system of claim 33, wherein said emergent behavior may comprise, but is not limited to, the following behaviors: synchronization, desynchronization, phase clustering, propagating waves, multi-cluster states, itinerant clustering, or other spatio-temporal phenomena.

37. The system of claim 33, wherein said measuring of the dynamic properties of the rhythmic elements could be performed through perturbation.

38. The system of claim 37, wherein said perturbation comprises using a pulse at every point along a rhythmic element's cycle.

39. The system of claim 37, wherein said perturbation comprises using feedback on one or more elements of the population.

40. The system of claim 33, wherein said measuring the dynamic properties of the rhythmic elements could be performed using two or more elements that are desynchronized but interacting and measuring their frequency shift as a function of their phase difference.

41. The system of claim 33, wherein said engineering system uses an external device, internal device, or any combination thereof.

42. The system of claim 41, wherein said external or internal device comprises:
  one or more input electrodes, one or more output electrodes, embedded control logic and memory, power management systems, and one or more external interfaces.

43. The system of claim 42, where said external interfaces are comprised of onboard interfaces, wired interfaces, or wireless interfaces.

44. The system of claim 33, wherein said reduced model comprises at least one of the following phase models: general dynamical models, Kuramoto Phase models, Winfree models, finite pulse models, integrate-and-fire models, and quadratic-integrate-and-fire models, or any combination thereof.

45. The system of claim 33, wherein said rhythmic elements comprises oscillators.

46. The system of claim 45, wherein said oscillators comprise at least one of the following: circadian rhythms, olfactory sensations, cardiac fibrillation, and cognitive processes, and tremors.

47. The system of claim 46, where said cognitive processes comprise those related to memory and visual perception.

48. The system of claim 47, where said tremors comprise Parkinson's disease-related tremors, epileptic seizures, and essential tremors.

49. The system of claim 45, wherein said oscillators comprise, but are not limited to, elements which undergo periodic or aperiodic fluctuations of physical quantities.

50. The system of claim 49, wherein said fluctuations of physical quantities comprise those found in: brain waves, laser elements, microwave elements, electrochemical elements, neurons, and cardiac muscle.

51. A computer program product comprising a non-transitory computer useable medium having computer program logic for enabling at least one processor in a computer system for engineering the emergent behavior of a target system having a population of rhythmic elements, said engineering emergent behavior method of said computer program logic comprising:
  receiving data from measuring means for measuring dynamic properties of the rhythmic elements;
  using a reduced model to determine target dynamical behavior of the system,
  determining perturbation that produces said target behavior, and wherein:
    said feedback comprises taking in a set of individual or aggregated signal measurements in order to construct a feedback loop,
    said determining said feedback further comprises preprocessing said taken in set of individual or aggregated signal measurements if necessary for the construction of said feedback,
    said preprocessing comprises a nonlinear mathematical transformation, and
    said nonlinear mathematical transformation is a time-delayed polynomial.

* * * * *